United States Patent
Aljuri et al.

(10) Patent No.: US 11,298,489 B2
(45) Date of Patent: **\*Apr. 12, 2022**

(54) METHODS AND DEVICES FOR PASSIVE RESIDUAL LUNG VOLUME REDUCTION AND FUNCTIONAL LUNG VOLUME EXPANSION

(71) Applicant: Pulmonx Corporation, Redwood City, CA (US)

(72) Inventors: Nikolai Aljuri, Hillsborough, CA (US); Rodney C. Perkins, Woodside, CA (US); Ryan Olivera, Granite Bay, CA (US); Hoang Nguyen, San Jose, CA (US); Srikanth Radhakrishnan, Cupertino, CA (US); Niyazi Beyhan, Santa Clara, CA (US)

(73) Assignee: Pulmonx Corporation, Redwood City, CA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 16/428,544

(22) Filed: May 31, 2019

(65) Prior Publication Data

US 2020/0038612 A1 Feb. 6, 2020

Related U.S. Application Data

(60) Continuation of application No. 14/703,670, filed on May 4, 2015, now Pat. No. 10,314,992, which is a
(Continued)

(51) Int. Cl.
*A61M 16/04* (2006.01)
*A61B 17/12* (2006.01)
(Continued)

(52) U.S. Cl.
CPC ....... *A61M 16/0434* (2013.01); *A61B 1/2676* (2013.01); *A61B 5/0084* (2013.01);
(Continued)

(58) Field of Classification Search
CPC ............ A61B 1/00082; A61B 1/00165; A61B 1/2676; A61B 10/02; A61B 17/12104;
(Continued)

(56) References Cited

U.S. PATENT DOCUMENTS 3,322,126 A   5/1967   Rusch et al.
3,498,286 A   3/1970   Michael et al.
(Continued)

FOREIGN PATENT DOCUMENTS

EP   0791340 A1   8/1997
EP   0815803 A1   1/1998
(Continued)

OTHER PUBLICATIONS

Notice of allowance dated Mar. 24, 2020 for U.S. Appl. No. 15/358,483.
(Continued)

*Primary Examiner* — Annette Dixon
(74) *Attorney, Agent, or Firm* — Wilson Sonsini Goodrich & Rosati

(57) ABSTRACT

The volume of a hyperinflated lung compartment is reduced by sealing a distal end of the catheter in an airway feeding the lung compartment. Air passes out of the lung compartment through a passage in the catheter while the patient exhales. A one-way flow element associated with the catheter prevents air from re-entering the lung compartment as the patient inhales. Over time, the pressure of regions surrounding the lung compartment cause it to collapse as the volume of air diminishes. Residual volume reduction effectively results in functional lung volume expansion. Option-
(Continued)

ally, the lung compartment may be sealed in order to permanently prevent air from re-entering the lung compartment. The invention further discloses a catheter with a transparent occlusion element at its tip that enables examination of the lung passageway through a viewing scope.

2 Claims, 12 Drawing Sheets

Related U.S. Application Data division of application No. 12/407,709, filed on Mar. 19, 2009, now Pat. No. 9,050,094, which is a continuation-in-part of application No. PCT/US2008/056706, filed on Mar. 12, 2008.

(51) Int. Cl.
| | | |
|---|---|---|
| *A61M 16/00* | (2006.01) | |
| *A61B 1/267* | (2006.01) | |
| *A61B 5/00* | (2006.01) | |
| *A61B 5/08* | (2006.01) | |
| *A61M 16/20* | (2006.01) | |
| *A61M 25/10* | (2013.01) | |
| *A61F 2/04* | (2013.01) | |

(52) U.S. Cl.
CPC .............. *A61B 5/08* (2013.01); *A61B 5/4836* (2013.01); *A61B 17/12104* (2013.01); *A61B 17/12136* (2013.01); *A61M 16/0003* (2014.02); *A61M 16/208* (2013.01); *A61F 2002/043* (2013.01); *A61M 16/0436* (2014.02); *A61M 25/10* (2013.01); *A61M 2016/003* (2013.01); *A61M 2016/0027* (2013.01); *A61M 2025/1052* (2013.01); *A61M 2202/0208* (2013.01); *A61M 2205/3334* (2013.01); *A61M 2207/10* (2013.01); *Y10T 29/49826* (2015.01)

(58) Field of Classification Search
CPC ... A61B 17/12136; A61B 18/08; A61B 18/24; A61B 2010/0074; A61B 2017/22054; A61B 2017/22059; A61B 2017/3435; A61B 2018/2238; A61B 5/0084; A61B 5/08; A61B 5/4836; A61F 2002/043; A61M 16/0003; A61M 16/04; A61M 16/0434; A61M 16/0436; A61M 16/0833; A61M 16/208; A61M 2016/0027; A61M 2016/003; A61M 2025/1052; A61M 2202/0208; A61M 2205/3334; A61M 2205/3368; A61M 2207/10; A61M 25/0119; A61M 25/10; A61M 3/0279; Y10S 128/26; Y10S 128/911; Y10S 128/912; Y10T 29/49826
See application file for complete search history.

(56) References Cited

U.S. PATENT DOCUMENTS

| | | | |
|---|---|---|---|
| 3,669,098 A | 6/1972 | Takahashi | |
| 3,677,262 A | 7/1972 | Zukowski | |
| 3,768,504 A | 10/1973 | Rentsch | |
| 3,776,222 A | 12/1973 | Smiddy | |
| 3,794,026 A | 2/1974 | Jacobs | |
| 3,866,599 A | 2/1975 | Johnson | |
| 3,913,568 A | 10/1975 | Carpenter | |
| 4,041,936 A | 8/1977 | Carden | |
| 4,134,407 A | 1/1979 | Elam | |
| 4,147,169 A | 4/1979 | Taylor | |
| 4,327,720 A | 5/1982 | Bronson et al. | |
| 4,327,721 A | 5/1982 | Goldin et al. | |
| 4,382,442 A | 5/1983 | Jones | |
| 4,453,545 A | 6/1984 | Inoue | |
| 4,468,216 A | 8/1984 | Muto | |
| 4,470,407 A * | 9/1984 | Hussein | A61B 1/00082 600/108 |
| 4,538,607 A | 9/1985 | Saul | |
| 4,567,882 A | 2/1986 | Heller | |
| 4,681,093 A | 7/1987 | Ono et al. | |
| 4,716,896 A | 1/1988 | Ackerman | |
| 4,742,819 A | 5/1988 | George | |
| 4,784,133 A | 11/1988 | Mackin | |
| 4,796,639 A | 1/1989 | Snow et al. | |
| 4,819,664 A | 4/1989 | Nazari | |
| 4,846,153 A | 7/1989 | Berci | |
| 4,850,371 A | 7/1989 | Broadhurst et al. | |
| 4,852,568 A | 8/1989 | Kensey | |
| 4,862,874 A | 9/1989 | Kellner | |
| 4,896,941 A | 1/1990 | Hayashi et al. | |
| 4,946,440 A * | 8/1990 | Hall | A61M 16/0833 604/164.09 |
| 4,949,716 A | 8/1990 | Chenoweth | |
| 4,955,375 A | 9/1990 | Martinez | |
| 4,958,932 A | 9/1990 | Kegelman et al. | |
| 4,961,738 A | 10/1990 | Mackin | |
| 4,976,710 A | 12/1990 | Mackin et al. | |
| 5,056,529 A | 10/1991 | De Groot et al. | |
| 5,143,062 A | 9/1992 | Peckham | |
| 5,146,916 A | 9/1992 | Catalani | |
| 5,165,420 A | 11/1992 | Strickland | |
| 5,181,913 A | 1/1993 | Erlich | |
| 5,246,012 A | 9/1993 | Strickland | |
| 5,285,778 A | 2/1994 | Mackin | |
| 5,308,325 A * | 5/1994 | Quinn | A61J 15/0015 604/174 |
| 5,309,903 A | 5/1994 | Long | |
| 5,329,940 A | 7/1994 | Adair | |
| 5,331,947 A | 7/1994 | Shturman et al. | |
| 5,361,753 A | 11/1994 | Pothmann et al. | |
| 5,439,444 A * | 8/1995 | Andersen | A61J 15/0015 156/60 |
| 5,447,165 A | 9/1995 | Gustafsson | |
| 5,477,851 A | 12/1995 | Callaghan et al. | |
| 5,499,625 A | 3/1996 | Frass et al. | |
| 5,546,935 A | 8/1996 | Champeau | |
| 5,573,005 A | 11/1996 | Ueda et al. | |
| 5,588,424 A | 12/1996 | Insler et al. | |
| 5,598,840 A | 2/1997 | Iund et al. | |
| 5,624,449 A | 4/1997 | Pham et al. | |
| 5,642,730 A | 7/1997 | Baran | |
| 5,645,519 A | 7/1997 | Lee et al. | |
| 5,653,231 A | 8/1997 | Bell | |
| 5,660,175 A | 8/1997 | Dayal | |
| 5,662,712 A | 9/1997 | Pathak et al. | |
| 5,682,880 A | 11/1997 | Brain | |
| 5,707,352 A | 1/1998 | Sekins et al. | |
| 5,752,921 A | 5/1998 | Orr | |
| 5,765,557 A | 6/1998 | Warters | |
| 5,795,322 A | 8/1998 | Boudewijn | |
| 5,800,455 A | 9/1998 | Palermo et al. | |
| 5,893,841 A | 4/1999 | Glickman | |
| 5,897,528 A | 4/1999 | Schultz | |
| 5,915,383 A * | 6/1999 | Pagan | A61M 16/0436 128/207.15 |
| 5,972,026 A | 10/1999 | Laufer et al. | |
| 5,997,546 A * | 12/1999 | Foster | A61J 15/0042 604/96.01 |
| 6,083,255 A | 7/2000 | Laufer et al. | |
| 6,099,546 A | 8/2000 | Gia | |
| 6,174,307 B1 | 1/2001 | Daniel et al. | |
| 6,174,323 B1 | 1/2001 | Biggs et al. | |
| RE37,117 E | 3/2001 | Palermo | |
| 6,258,100 B1 | 7/2001 | Alferness et al. | |
| 6,287,290 B1 | 9/2001 | Perkins et al. | |
| 6,293,951 B1 | 9/2001 | Alferness et al. | |
| 6,346,074 B1 | 2/2002 | Roth | |
| 6,398,775 B1 | 6/2002 | Perkins et al. | |
| 6,527,761 B1 | 3/2003 | Soltesz et al. | |
| 6,585,639 B1 | 7/2003 | Kotmel et al. | |

(56) References Cited

U.S. PATENT DOCUMENTS

| | | |
|---|---|---|
| 6,609,521 B1 | 8/2003 | Belani et al. |
| 6,629,951 B2 | 10/2003 | Laufer et al. |
| 6,651,672 B2 | 11/2003 | Roth et al. |
| 6,679,264 B1 | 1/2004 | Deem et al. |
| 6,692,494 B1 | 2/2004 | Cooper et al. |
| 6,709,401 B2 | 3/2004 | Perkins et al. |
| 6,712,812 B2 | 3/2004 | Roschak et al. |
| 6,722,360 B2 | 4/2004 | Doshi |
| 6,749,606 B2 | 6/2004 | Keast et al. |
| 6,792,947 B1 | 9/2004 | Bowden |
| 6,878,141 B1 | 4/2005 | Perkins et al. |
| 6,886,558 B2 | 5/2005 | Tanaka |
| 6,941,950 B2 | 9/2005 | Wilson et al. |
| 6,997,189 B2 | 2/2006 | Biggs et al. |
| 6,997,918 B2 | 2/2006 | Soltesz et al. |
| 7,011,094 B2 | 3/2006 | Rapacki et al. |
| 7,022,088 B2 | 4/2006 | Keast et al. |
| 7,086,398 B2 | 8/2006 | Tanaka |
| 7,276,077 B2 | 10/2007 | Zadno-Azizi et al. |
| 7,449,010 B1 | 11/2008 | Hayase et al. |
| 7,588,033 B2 | 9/2009 | Wondka |
| 7,744,594 B2* | 6/2010 | Yamazaki .......... A61B 18/1492 606/41 |
| 7,819,840 B2* | 10/2010 | Burnside .......... A61M 25/1029 604/101.01 |
| 7,883,471 B2 | 2/2011 | Aljuri et al. |
| 8,137,302 B2 | 3/2012 | Aljuri et al. |
| 8,551,043 B2* | 10/2013 | Crooms .......... A61J 15/0042 604/103 |
| 9,050,094 B2* | 6/2015 | Aljuri .......... A61M 16/208 |
| 9,533,116 B2 | 1/2017 | Aljuri et al. |
| 10,314,992 B2* | 6/2019 | Aljuri .......... A61B 5/4836 |
| 2001/0051899 A1 | 12/2001 | Kawashima et al. |
| 2002/0049370 A1 | 4/2002 | Laufer et al. |
| 2002/0062120 A1 | 5/2002 | Perkins et al. |
| 2002/0169413 A1 | 11/2002 | Keren et al. |
| 2003/0051733 A1 | 3/2003 | Kotmel et al. |
| 2003/0171332 A1 | 9/2003 | Abraham et al. |
| 2003/0228344 A1 | 12/2003 | Fields et al. |
| 2004/0016435 A1 | 1/2004 | Deem et al. |
| 2004/0220556 A1 | 11/2004 | Cooper et al. |
| 2004/0243016 A1 | 12/2004 | Sanderson et al. |
| 2005/0016530 A1 | 1/2005 | McCutcheon et al. |
| 2005/0022809 A1 | 2/2005 | Wondka |
| 2005/0187561 A1 | 8/2005 | Lee-Sepsick et al. |
| 2005/0288684 A1 | 12/2005 | Aronson et al. |
| 2006/0095002 A1 | 5/2006 | Soltesz et al. |
| 2006/0102186 A1 | 5/2006 | Adler |
| 2006/0122647 A1 | 6/2006 | Callaghan et al. |
| 2006/0129134 A1 | 6/2006 | Kerr |
| 2006/0264772 A1 | 11/2006 | Aljuri et al. |
| 2006/0283462 A1 | 12/2006 | Fields et al. |
| 2007/0005083 A1 | 1/2007 | Saban et al. |
| 2007/0096048 A1 | 5/2007 | Clerc |
| 2007/0142742 A1 | 6/2007 | Aljuri et al. |
| 2007/0225747 A1 | 9/2007 | Perkins et al. |
| 2008/0051719 A1 | 2/2008 | Nair et al. |
| 2008/0228130 A1 | 9/2008 | Aljuri et al. |
| 2008/0228137 A1 | 9/2008 | Aljuri et al. |
| 2009/0241964 A1 | 10/2009 | Aljuri et al. |
| 2009/0260625 A1 | 10/2009 | Wondka |
| 2010/0031964 A1 | 2/2010 | Turek et al. |
| 2011/0011406 A1 | 1/2011 | Blom et al. |
| 2011/0152678 A1 | 6/2011 | Aljuri et al. |
| 2011/0203594 A1 | 8/2011 | Brain |
| 2011/0259339 A1 | 10/2011 | Isaza |
| 2017/0071606 A1 | 3/2017 | Aljuri et al. |

FOREIGN PATENT DOCUMENTS

| | | |
|---|---|---|
| EP | 0982044 A2 | 3/2000 |
| EP | 1078601 B1 | 10/2006 |
| JP | 2004504867 A | 2/2004 |
| WO | WO-9210971 A1 | 7/1992 |
| WO | WO-9533506 A1 | 12/1995 |
| WO | WO-9844854 A1 | 10/1998 |
| WO | WO-9848706 A1 | 11/1998 |
| WO | WO-9849191 A1 | 11/1998 |
| WO | WO-9901076 A1 | 1/1999 |
| WO | WO-9917827 A2 | 4/1999 |
| WO | WO-9920332 A1 | 4/1999 |
| WO | WO-9932040 A1 | 7/1999 |
| WO | WO-9934741 A1 | 7/1999 |
| WO | WO-9964109 A1 | 12/1999 |
| WO | WO-0041612 A2 | 7/2000 |
| WO | WO-0051510 A1 | 9/2000 |
| WO | WO-0062699 A2 | 10/2000 |
| WO | WO-0102042 A1 | 1/2001 |
| WO | WO-0103642 A1 | 1/2001 |
| WO | WO-0110314 A2 | 2/2001 |
| WO | WO-0113839 A1 | 3/2001 |
| WO | WO-0113908 A2 | 3/2001 |
| WO | WO-03022124 A2 | 3/2003 |
| WO | WO-03022221 A2 | 3/2003 |
| WO | WO-2006055692 A2 | 5/2006 |
| WO | WO-2006078451 A2 | 7/2006 |
| WO | WO-2006091597 A1 | 8/2006 |

OTHER PUBLICATIONS

Office action dated Oct. 2, 2019 for U.S. Appl. No. 15/358,483.

Becker et al., Lung Volumes Before and After Lung Volume Reduction Surgery, Am J Respir Crit Care Med, 1998; 157:1593-1599.

Criner et al., Effect of Lung Volume Reduction Surgery on Diaphragm Strength, Am J Respir Crit Care Med, 1998; 157:1578-1585.

"European search report and opinion dated Oct. 13, 2015 for EP Application No. 08732032.1."

European search report and opinion dated Nov. 16, 2009 for EP Application No. 06717427.6.

"Final Office action dated Oct. 11, 2018 for U.S. Appl. No. 14/703,670".

Harada et al., Re-expansion of Refractory Atelectasis Using a Bronchofiberscope with a Balloon Cuff, Chest, Dec. 1983; 84:725-728.

International search report and written opinion dated Aug. 26, 2008 for PCT/US2008/056706.

Kotloff et al., "Comparison of Short-term Functional Outcomes Following Unilateral and Bilateral Lung Volume Reduction Surgery," Chest. Apr. 1998;113(4):890-5.

Morrell et al., "Collateral ventilation and gas exchange during airway occlusion in the normal human lung," Am Rev Respir Dis. Mar. 1993;147(3):535-539.

"Notice of allowance dated Jan. 27, 209 for U.S. Appl. No. 14/706,670".

Notice of allowance dated Feb. 2, 2015 for U.S. Appl. No. 12/407,709.

"Notice of allowance dated Mar. 26, 2013 for U.S. Appl. No. 12/820,547."

Notice of Allowance dated Aug. 26, 2016 for U.S. Appl. No. 13/938,025.

"Office action dated Apr. 10, 2015 for U.S. Appl. No. 13/938,025."

Office action dated Apr. 11, 2012 for U.S. Appl. No. 12/407,709.

Office action dated Apr. 15, 2010 for U.S. Appl. No. 11/685,008.

Office action dated Jul. 8, 2014 for U.S. Appl. No. 12/407,709.

Office action dated Aug. 1, 2012 for U.S. Appl. No. 12/820,547.

Office action dated Nov. 1, 2013 for U.S. Appl. No. 12/407,709.

Office action dated Nov. 24, 2009 for U.S. Appl. No. 11/685,008.

Office action dated Dec. 17, 2012 for U.S. Appl. No. 12/407,709.

Office action dated Dec. 18, 2015 for U.S. Appl. No. 13/938,025.

Ojo et al., Lung volume reduction surgery alters management of pulmonary nodules in patients with severe COPD. Chest. Dec. 1997; 112(6): 1494-1500.

Sclafani, "Clearing the Airways," AARC Times, Jan. 1999, pp. 69-72.

Snell, et al. The potential for bronchoscopic lung volume reduction using bronchial prostheses. Chest. Sep. 2003; 124(3):1073-1080.

U.S. Appl. No. 11/428,762, filed Jul. 5, 2006.

(56) References Cited

OTHER PUBLICATIONS

U.S. Appl. No. 60/828,496, filed Oct. 26, 2006.
U.S. Appl. No. 14/703,670 Office Action dated Jan. 31, 2018.
Woolcock et al., Mechanical Factors Influencing Collateral Ventilation In Human, Dog, and Pig Lungs, J Appl Physiol. Jan. 1971; 30(1):99-115.

* cited by examiner

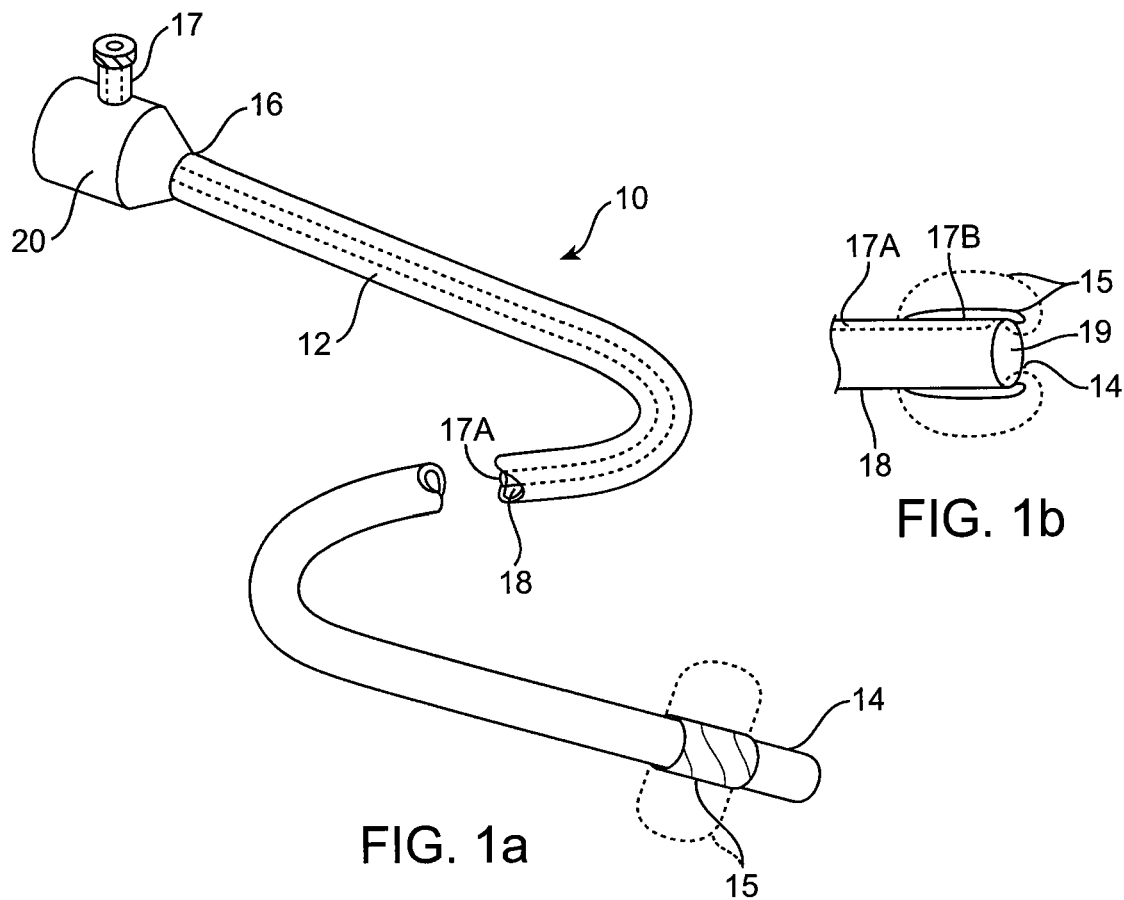
FIG. 1b
FIG. 1a
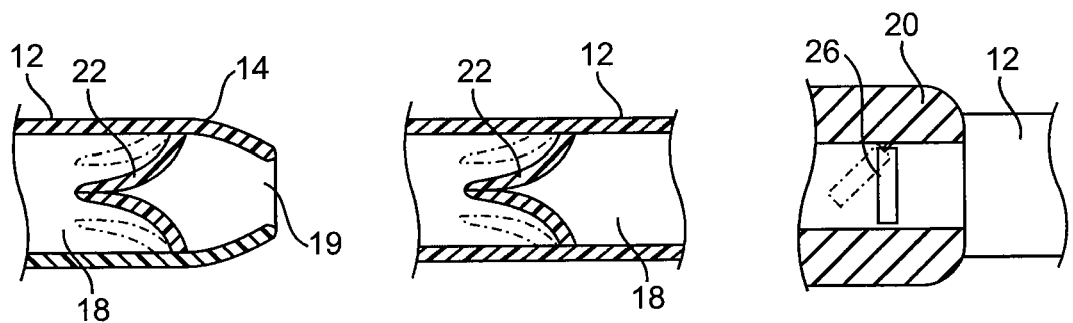
FIG. 2    FIG. 3    FIG. 4

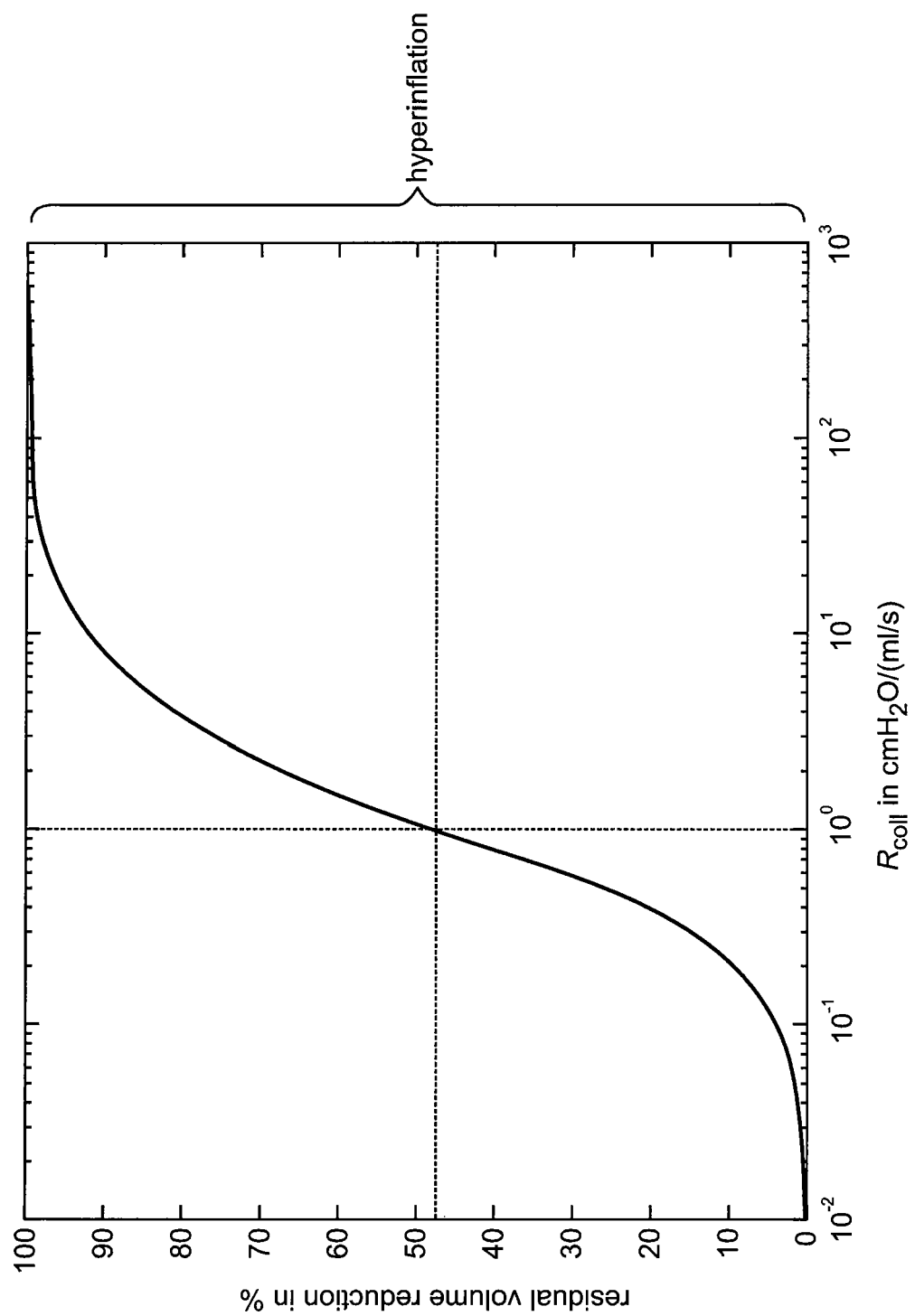

METHODS AND DEVICES FOR PASSIVE RESIDUAL LUNG VOLUME REDUCTION AND FUNCTIONAL LUNG VOLUME EXPANSION

CROSS-REFERENCE TO RELATED APPLICATION

The present application is a continuation of U.S. patent application Ser. No. 14/703,670, filed May 4, 2015, now U.S. Pat. No. 10,314,992, which is a divisional of U.S. patent application Ser. No. 12/407,709, filed Mar. 19, 2009 (now U.S. Pat. No. 9,050,094), which is a continuation-in-part of International Application No. PCT/US08/56706, filed Mar. 12, 2008, which claims the benefit of U.S. patent application Ser. No. 11/685,008, filed, Mar. 12, 2007, the full disclosures of which are incorporated herein by reference.

BACKGROUND OF THE INVENTION

1. Field of the Invention

The present invention relates generally to medical methods and apparatus. More particularly, the present invention relates to methods and apparatus for endobronchial residual lung volume reduction by passive deflation of hyperinflated segments with functional lung volume expansion as a result.

Chronic obstructive pulmonary disease is a significant medical problem affecting 16 million people or about 6% of the U.S. population. Specific diseases in this group include chronic bronchitis, asthmatic bronchitis, and emphysema. While a number of therapeutic interventions are used and have been proposed, none are completely effective, and chronic obstructive pulmonary disease remains the fourth most common cause of death in the United States. Thus, improved and alternative treatments and therapies would be of significant benefit.

Of particular interest to the present invention, lung function in patients suffering from some forms of chronic obstructive pulmonary disease can be improved by reducing the effective lung volume, typically by resecting diseased portions of the lung. Resection of diseased portions of the lungs both promotes expansion of the non-diseased regions of the lung and decreases the portion of inhaled air which goes into the lungs but is unable to transfer oxygen to the blood. Lung volume reduction is conventionally performed in open chest or thoracoscopic procedures where the lung is resected, typically using stapling devices having integral cutting blades.

While effective in many cases, conventional lung volume reduction surgery is significantly traumatic to the patient, even when thoracoscopic procedures are employed. Such procedures often result in the unintentional removal of healthy lung tissue, and frequently leave perforations or other discontinuities in the lung which result in air leakage from the remaining lung. Even technically successful procedures can cause respiratory failure, pneumonia, and death. In addition, many older or compromised patients are not able to be candidates for these procedures.

As an improvement over open surgical and minimally invasive lung volume reduction procedures, endobronchial lung volume reduction procedures have been proposed. For example, U.S. Pat. Nos. 6,258,100 and 6,679,264 describe placement of one-way valve structures in the airways leading to diseased lung regions. It is expected that the valve structures will allow air to be expelled from the diseased region of the lung while blocking reinflation of the diseased region. Thus, over time, the volume of the diseased region will be reduced and the patient condition will improve.

While promising, the use of implantable, one-way valve structures is problematic in at least several respects. The valves must be implanted prior to assessing whether they are functioning properly. Thus, if the valve fails to either allow expiratory flow from or inhibit inspiratory flow into the diseased region, that failure will only be determined after the valve structure has been implanted, requiring surgical removal. Additionally, even if the valve structure functions properly, many patients have diseased lung segments with collateral flow from adjacent, healthy lung segments. In those patients, the lung volume reduction of the diseased region will be significantly impaired, even after successfully occluding inspiration through the main airway leading to the diseased region, since air will enter collaterally from the adjacent healthy lung region. When implanting one-way valve structures, the existence of such collateral flow will only be evident after the lung region fails to deflate over time, requiring further treatment.

For these reasons, it would be desirable to provide improved and alternative methods and apparatus for effecting residual lung volume reduction in hyperinflated and other diseased lung regions. The methods and apparatus will preferably allow for passive deflation of an isolated lung region without the need to implant a one-way valve structure in the lung. The methods and apparatus will preferably be compatible with known protocols for occluding diseased lung segments and regions after deflation, such as placement of plugs and occluding members within the airways leading to such diseased segments and regions. Additionally, such methods and devices should be compatible with protocols for identifying and treating patients having diseased lung segments and regions which suffer from collateral flow with adjacent healthy lung regions. At least some of these objectives will be met by the inventions described hereinbelow.

2. Description of the Related Art

Methods for performing minimally invasive and endobronchial lung volume reduction are described in the following U.S. Pat. Nos. 5,972,026; 6,083,255; 6,258,100; 6,287,290; 6,398,775; 6,527,761; 6,585,639; 6,679,264; 6,709,401; 6,878,141; 6,997,918; 2001/0051899; and 2004/0016435. Balloon catheter devices for use in body passageways have previously been described in U.S. Pat. Nos. 4,976,710; 4,470,407; 4,681,093 and 6,174,307, and. U.S. Pat. No. 4,976,710 describes an angioscope with a transparent occlusion balloon at its distal end. Similarly, U.S. Pat. No. 6,174,307 describes an endovascular catheter with a transparent portion near the distal tip that can be used to view the body passageway. Similarly, issued U.S. Pat. Nos. 4,470,407 and 4,681,093 also describe endovascular devices with a transparent expandable balloon covering the lens. Though these catheters utilize the balloons to view the passageways, their use for viewing pulmonary passageways is limited in several aspects. Practically, the use of these devices in pulmonary passageways would be limited to those passageways large enough to accommodate a similarly constructed bronchoscope. These devices are also limited by the fact that treatment is limited to the exact site of visualization, rather than at a point distal to the visualization point. Further, the flexibility of these devices would be limited by the inherent properties of a visualization catheter. Hence, it would be beneficial to have a catheter that is flexible and to use it to visualize points that are distal to the location of the distal tip of the catheter.

SUMMARY OF THE INVENTION

The present invention provides methods and apparatus for passively reducing the residual volume (the volume of air remaining after maximal exhalation) of hyperinflated or otherwise diseased lung compartments or segments. By "passively reducing," it is meant that air can be removed from the diseased lung region without the use of a vacuum aspiration to draw the air from the region. Typically, such passive reduction will rely on a non-implanted one-way flow element, structure, or assembly which permits air to be exhaled or exhausted from the lung region while preventing or inhibiting the inspiration of air back into the lung region. By non-implanted, it is meant that some portion of the element, structure, or assembly will be temporarily placed in an airway or bronchus leading to the lung region in a manner that allows that portion to be removed later, typically within days or hours, without the need for surgical intervention Thus, the methods of the present invention will not require the permanent implantation of valves or other structures prior to actually achieving the desired residual lung volume reduction, as with the one-way implantable valve structures of the prior art.

The methods and apparatus of the present invention can be terminated and all apparatus removed should it appear for any reason that the desired residual lung volume reduction is not being achieved. Commonly, such failure can be the result of collateral flow into the diseased lung region from adjacent healthy lung region(s). In such cases, steps can be taken to limit or stop the collateral flow and allow resumption of the passive lung volume reduction protocols. In other cases, it might be desirable or necessary to employ open surgical, thoracoscopic, or other surgical procedures for lung resection.

Patients who successfully achieve residual volume reduction of hyperinflated or other diseased lung regions in accordance with the principles of the present invention will typically have those regions sealed permanently to prevent reinflation. Such sealing can be achieved by a variety of known techniques, including the application of radiofrequency or other energy for shrinking or sealing the walls of the airways feeding the lung region. Alternatively, synthetic or biological glues could be used for achieving sealing of the airway walls. Most commonly, however, expandable plugs will be implanted in the airways leading to the deflated lung region to achieve the sealing.

In a first aspect of the present invention, methods for reducing the residual volume of a hyperinflated lung compartment comprise sealingly engaging a distal end of a catheter in an airway feeding the lung compartment. Air is allowed to be expelled from the lung compartment through a passage in the catheter while the patient is exhaling, and air is blocked from re-entering the lung compartment through the catheter passage while the patient is inhaling. As the residual volume diminishes, the hyperinflated lung compartment reduces in size freeing up the previously occupied space in the thoracic cavity. Consequently, a greater fraction of the Total Lung Capacity (TLC), which is the volumetric space contained in the thoracic cavity that is occupied by lung tissue after a full inhalation becomes available for the healthier lung compartments to expand and the volume of the lung available for gas exchange commonly referred to in clinical practice as the lung's Functional Vital Capacity (FVC) or Vital Capacity (VC) increases, the result of which is effectively a functional lung volume expansion.

The hyperinflated lung compartment will usually be substantially free of collateral flow from adjacent lung compartments, and optionally the patient can be tested for the presence of such collateral flow, for example using techniques taught in copending, commonly assigned application Ser. No. 11/296,951, filed on Dec. 7, 2005; Ser. No. 11/550,660, filed on Oct. 18, 2006; and application Ser. No. 11/428,762, filed on Jul. 5, 2006, the full disclosures of which are incorporated herein by reference.

Alternatively, the methods of the present invention for reducing residual lung volume can be performed in patients having collateral flow channels leading into the hyperinflated or other diseased lung compartment. In such cases, the collateral flow channels may first be blocked, for example, by introducing glues, occlusive particles, hydrogels or other blocking substances, as taught for example in copending application Ser. No. 11/684,950, filed on Mar. 12, 2008, the full disclosure of which is incorporated herein by reference. In other cases, where the flow channels are relatively small, those channels will partially or fully collapse as the residual lung volume is reduced. In such cases, the patient may be treated as if the collateral flow channels did not exist. The effectiveness of reduction in hyperinflation however will depend on the collateral resistance between the hyperinflated compartment and the neighboring compartments, as illustrated in FIG. 9, where residual volume reduction is negligible when the resistance to collateral flow Rcoll is very small (significant collateral flow channels) and maximally effective when Rcoll is very high (no collateral flow channels).

In all of the above methods, it may be desirable to introduce an oxygen-rich gas into the lung compartment while or after the lung volume is reduced in order to induce or promote absorption atelectasis. Absorption atelectasis promotes absorption of the remaining or residual gas in the compartment into the blood to further reduce the volume, either before or after permanent sealing of the lung volume compartment or segment.

In a second aspect, the present invention provides catheters for isolating and deflating hyperinflated and other diseased lung compartments. The catheter comprises a catheter body, an expandable occluding member on the catheter body, and a one-way flow element associated with the catheter body. The catheter body usually has a distal end, a proximal end, and at least one lumen extending from a location at or near the distal end to a location at or near the proximal end. At least a distal portion of the catheter body is adapted to be advanced into and through the airways of a lung so that the distal end can reach an airway which feeds a target lung compartment or segment to be treated. The expandable occluding member is disposed at or near the distal end of the catheter body and is adapted to be expanded in the airway which feeds the target lung compartment or segment so that said compartment or segment can be isolated with access provided only through the lumen or catheter body when the occluding member is expanded.

The catheter of the present invention can be used in conjunction with, or independent of, a viewing scope such as a bronchoscope. Since it is generally configured to be narrower than a visualization tube such as a bronchoscope, the catheter may be introduced into narrower passageways and is used to isolate a portion of lung tissue.

In one embodiment of the catheter, the expandable occluding element is disposed near the distal end of the catheter body. In this embodiment, the expandable occluding element is configured such that both the proximal and distal ends of the expandable occluding element are attached to the outer surface of the catheter body.

In another embodiment of the catheter, the expandable occluding element is disposed at the distal end of the catheter body, and is configured to form a cover over the rim of the lumen. This embodiment prevents or inhibits entry of mucus into the lumen, and prevents the catheter tip from contacting the airway wall. A method of manufacturing this embodiment of the catheter is also disclosed. One end of the occluding element is attached to the internal surface of the central passageway at the tip of the catheter. The occluding element is then inverted over the catheter body and a second end of the occluding element is attached to the outer surface of the catheter body. The expandable occluding element is optionally transparent to enable viewing the body passageway (for example during diagnostic or treatment procedures).

The one-way flow element is adapted to be disposed within or in-line with the lumen of the catheter body in order to allow flow in a distal-to-proximal direction so that air will be expelled from the isolated lung compartment or segment as the patient exhales. The one-way flow element, however, inhibits or prevents flow through the lumen in a proximal-to-distal direction so that air cannot enter the isolated lung compartment or segment while the patient is inhaling.

For the intended endobronchial deployment, the catheter body will typically have a length in the range from 20 cm to 200 cm, preferably from 80 cm to 120 cm, and a diameter near the distal end in the range from 0.1 mm to 10 mm, preferably from 1 mm to 5 mm. The expandable occluding member will typically be an inflatable balloon or cuff, where the balloon or cuff has a width in the range from 1 mm to 30 mm, preferably from 5 mm to 20 mm, when inflated. The one-way flow element is typically a conventional one-way flow valve, such as a duck-bill valve, a flap valve, or the like, which is disposed in the lumen of the catheter body, either near the distal end or at any other point within the lumen. Alternatively, the one-way flow element could be provided as a separate component, for example, in a hub which is detachably mounted at the proximal end of the catheter body. In other instances, it might be desirable to provide two or more one-way flow elements in series within the lumen or otherwise provided in-line with the lumen in order to enhance sealing in the inspiratory direction through the lumen. In a particular illustrated embodiment, a one-way flow control assembly is provided as part of an external console attached in-line with the catheter lumen. The flow-control assembly comprises a valve that is controlled electrically or through other means, sensors for sensing flow and pressure in the lumen, and a valve controller for controlling the valve based on input from the sensors. The sensors monitor flow to detect the beginning of an inhalation cycle and pressure to detect the beginning of an exhalation cycle. Based on the input from the sensors, the valve controller opens the valve at the beginning of the exhalation cycle to deflate the lung region and closes the valve at the beginning of the inhalation cycle to prevent reinflation of the lung region.

BRIEF DESCRIPTION OF THE DRAWINGS

FIG. 1a is a perspective view of an isolation and deflation catheter constructed in accordance with the principles of the present invention.

FIG. 1b illustrates an embodiment of the occluding element covering the distal end of the catheter.

FIGS. 2-4 illustrate alternative placements of one-way flow elements within a central lumen of the catheter of FIG. 1.

FIG. 5b shows an external console housing the one-way flow element shown in FIG. 5a.

FIG. 6a shows a flowchart and FIG. 6b show flow and pressure graphs, illustrating the operation of the one-way flow element shown in FIG. 5a.

FIG. 9 is a graph showing the relationship between collateral resistance Rcoll and residual volume reduction in an isolated lung compartment.

DETAILED DESCRIPTION OF THE INVENTION

Figure 1C:
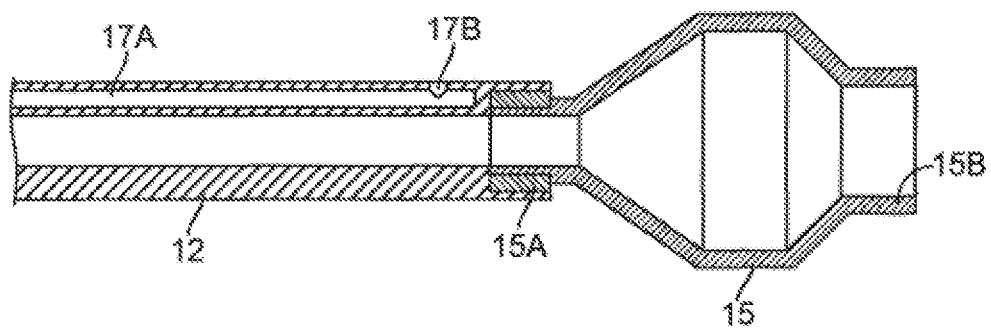
FIGS. 1c and 1d show a method of manufacture of the embodiment of the occluding element shown in FIG. 1b.

Referring to FIGS. 1a and 1b, an endobronchial lung volume reduction catheter 10 constructed in accordance with the principles of the present invention includes an elongate catheter body 12 having a distal end 14 and a proximal end 16. Catheter body 12 includes at least one lumen 18 or central passage extending generally from the distal end 14 to the proximal end 16. Lumen 18 will have a distal opening 19 at or near the distal end 14 in order to permit air or other lung gases to enter the lumen and flow in a distal-to-proximal direction out through the proximal end of the lumen. Additionally, catheter body 12 will have an expandable occluding element 15 at or near the distal end 14, to occlude an air passageway during treatment.

As mentioned above, in one embodiment the expandable occluding element 15 is disposed near the distal end of the catheter body to seal the passageway, while in an alternate embodiment the expandable occluding element 15 forms a cover of the rim of the catheter lumen in order to seal the passageway, prevent or inhibit mucus entry into the lumen, and shield the passageway wall from the tip of the catheter. In the alternate embodiment, the expandable occluding element 15 may be transparent to allow viewing of the passageway. These embodiments will now be described in more detail with reference to the Figures.

In one embodiment of the catheter, as shown in FIG. 1a, the expandable occluding element 15 is located at or near the distal end 14. In this embodiment, the expandable occluding element 15 is configured such that the proximal and distal ends of the expandable occluding element 15 are attached to the outer surface of the catheter body 12. An inflation lumen 17A extends from the inflation port 17B to the expandable occluding element 15 to provide for expansion of the expandable occluding element 15.

In an alternate embodiment, as shown in FIG. 1b, the expandable occluding element 15 is disposed at the distal end of the catheter body 12, and is configured to form a cover over the rim of the distal opening 19 of the catheter body 12. In this embodiment, the proximal end of the expandable occluding element 15 is attached to the outer surface of the catheter body 12, while the inner surface of the expandable occluding element 15 wraps over the rim of the catheter body 12 and is attached to the inner surface of the catheter body 12. Inflation lumen 17A is used to inflate the expandable occluding element 15 through inflation port 17B. When inflated, the expandable occluding element 15 will form a cover (or "lip"), over the rim of the catheter body 12, thereby preventing or inhibiting entry of mucus into the lumen 18 of the catheter, and preventing or inhibiting the opening 19 from contacting the walls of the passageway. The inflated expandable occluding element 15 also helps prevent or inhibit accidental placement of the catheter tip into an airway segment that is smaller than the intended airway segment. Additionally or optionally, the expandable occluding element 15 and the distal portion of the catheter body 12 comprise a transparent material to enable viewing past the expandable occluding element 15.

Figure 1D:
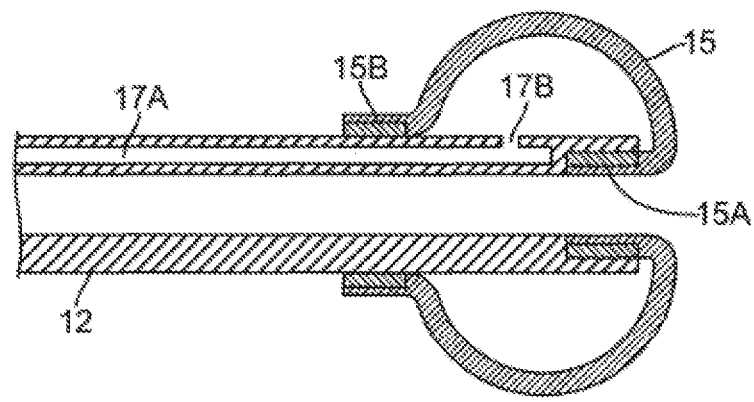

Manufacture of the second embodiment of the catheter 10 is shown in FIGS. 1c and 1d. As shown in FIG. 1c, one end 15A of the expandable occluding element 15 is circumferentially attached to the inner wall of the lumen, using any suitable technique such as thermal bonding or adhesive bonding. Then, the expandable occluding element 15 is inverted over the catheter tip and catheter body 12, as shown in FIG. 1d. The second end 15B of the expandable occluding element 15, which is now proximal to the tip of the catheter, is attached circumferentially to the outer surface of the catheter body 12, using any suitable technique such as thermal bonding or adhesive bonding. The expandable occluding element 15 thus encloses the outer rim of the distal end of the catheter. Further, the expandable occluding element 15 is configured such that it is fed for inflation by an inflation port 17B leading from an inflation lumen 17A. Though the figures describe a preformed balloon-like expandable occluding element 15, any suitable material of any shape may be used to manufacture the expandable occluding element 15 in the described manner, as should be obvious to one of ordinary skill in the art. For example, as described above, some portion of the catheter body 12 and/or of the expandable occluding element 15 may be configured to be transparent. Optionally, a hub 20 will be provided at the proximal end, for example as shown in FIG. 1a, but the hub is not a necessary component of the catheter.

Additionally and optionally, catheter 10 is configured to be introducible into the passageway via a viewing scope such as a bronchoscope (not shown). Use of the scope, in conjunction with a catheter 10 comprising one or more transparent components as described above, enables enhanced viewing of the body passageway during diagnostic or treatment procedures, by allowing a user to view the body passageway through the transparent expandable occluding element 15. Additionally, a transparent expandable occluding element 15 could serve as a lens to be used in conjunction with the scope. When so used, light from the scope would interact with the expandable occluding element 15 in such a manner as to enable more enhanced viewing than would be obtained without the use of a transparent expandable occluding element 15. Examples of such enhanced viewing could include: obtaining wide angle or fish-eye views or a greater field of vision, telephoto properties (macro, zoom, etc.) or color filtration. These can be achieved by manipulating the material properties of the expandable occluding element 15.

The technique of using a transparent, expandable element on a catheter may also be used independently. For example, in one embodiment, a catheter may be equipped with a transparent expandable occluding element 15 similar to that shown in FIG. 1b. In such an embodiment, the transparent expandable occluding element 15 serves as an image enhancer or diagnostic lens, and need not be fully occlusive. Similar to the above description, when used in conjunction with a viewing scope, it would enable more enhanced diagnostic viewing than would be obtained without the use of a transparent expandable occluding element 15. Examples of such enhanced viewing could include: obtaining wide angle or fish-eye views or a greater field of vision, telephoto properties (macro, zoom, etc.) or color filtration. These can be achieved by manipulating the material properties of the transparent expandable occluding element 15. Additionally, the transparent expandable occluding element 15 may be configured to allow for therapeutic procedures, such as delivery of a therapeutic electromagnetic energy (e.g., laser, infrared, etc.) to the lung or other tissue. In such a case, the surface, shape, material, size or other properties of the lens can be chosen to allow a user to manipulate the therapeutic laser energy. For example a user could focus or diffuse the energy by moving the source of laser energy back and forth relative to the transparent expandable occluding element 15.

The present invention relies on placement of a one-way flow element within or in-line with the lumen 18 so that flow from an isolated lung compartment or segment (as described hereinbelow) may occur in a distal-to-proximal direction but flow back into the lung compartment or segment is inhibited or blocked in the proximal-to-distal direction. As shown in FIGS. 2-4, a one-way flow element 22 may be provided in the lumen 18 near the distal end 14 of the catheter body 12, optionally being immediately proximal of the distal opening 19. As shown, the one-way flow element 22 is a duck-bill valve which opens as shown in broken line as the patient exhales to increase the pressure on the upstream or distal side of the one-way flow element 22. As the patient inhales, the pressure on the upstream or distal side of the valve is reduced, drawing the valve leaflets closed as shown in full line.

Alternatively or additionally, the one-way flow element 22 could be provided anywhere else in the lumen 18, and two, three, four, or more such valve structures could be included in order to provide redundancy.

As a third option, a one-way valve structure 26 in the form of a flap valve could be provided within the hub 20. The hub 20 could be removable or permanently fixed to the catheter body 12. Other structures for providing in-line flow control could also be utilized, as will be presently described.

In addition to the passive one-way valve structures described above, one-way flow functionality may be provided using an actively controlled one-way flow control assembly. One-way flow can be controlled by measuring the flow and pressure through the lumen and using this information to determine the beginning and end of inhalation and exhalation cycles and thereby determining whether the valve should remain open or closed. In one embodiment, the one-way flow control assembly is provided as part of an external console attached in-line with the catheter lumen. The console comprises a channel for air flow to which the proximal end of the catheter connects via a standard connector. When the patient exhales, air is forced through the catheter lumen into the console's air channel, and then exits through an exhaust port of the console. The one-way flow control assembly comprises a valve that is within or in-line with the catheter lumen and can be opened or closed by a valve controller to control the air flow through the air channel. The valve controller opens and closes the valve based on input from flow and pressure sensors within or in-line with the catheter lumen. The sensors measure the air flow and air pressure to detect the inhalation and exhalation cycles of the patient. Based on input from the sensors, the valve controller opens the valve at the beginning of the exhalation cycle, and closes the valve at the beginning of the inhalation cycle. The valve controller may control the valve electrically, magnetically, mechanically or through other means known in the art.

Figure 5A:
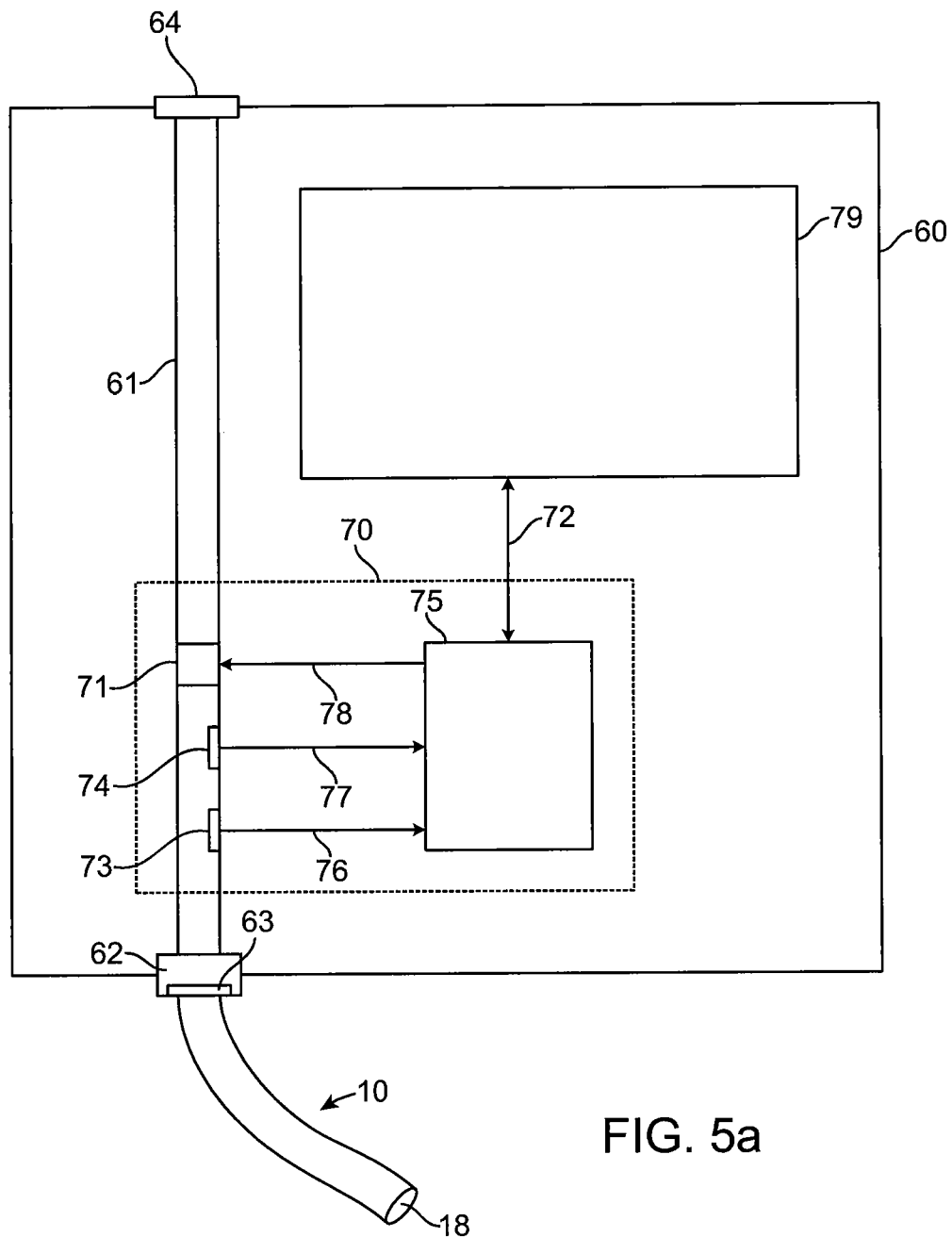
FIG. 5a shows an alternative embodiment of a one-way flow element comprising a valve controller coupled to sensors and an electrically-controlled valve.

FIG. 5a shows an illustration of such an actively controlled one-way flow control assembly provided as part of an external console. The external console 60 comprises an air channel 61, a connector 62, and an exhaust port 64. Catheter 10 is detachably coupled to air channel 61 using a standard connector 62, such that air channel 61 is in-line with lumen 18. Preferably, a filter 63 is provided between the air channel 61 and lumen 18 to maintain sterility of air channel 61 and promote reusability of console 60. Additionally, air flowing into air channel 61 is expelled through exhaust port 64. Console 60 comprises a one-way flow assembly 70 in-line with lumen 18 of catheter 10.

One-way flow assembly 70 comprises an electrically controlled valve 71, a flow sensor 73, a pressure sensor 74, and a valve controller 75. In one embodiment, valve 71, flow sensor 73, and pressure sensor 74 are disposed within air channel 61. Valve controller 75 provides one-way flow functionality by opening and closing valve 71 based on flow and pressure signals received from sensors 73 and 74, respectively. When valve 71 is closed, it prevents air from flowing into the lumen of catheter 10 (during inhalation); during exhalation, valve 71 remains open and allows air to flow out of the isolated lung compartment.

In one embodiment, valve 71 is a solenoid-based valve. Alternatively, valve 71 may be any other valve that can be opened and closed via an electrical control signal. Flow sensor 73 and pressure sensor 74, respectively, measure air flow and pressure in lumen 18. Valve controller 75 receives a flow indicator signal 76 from the flow sensor 73 and a pressure indicator signal 77 from pressure sensor 74 and produces a valve control signal 78 to open or close valve 71. Alternatively, one or more of flow sensor 73, pressure sensor 74, and valve 71 may reside within lumen 18 and be in communication with valve controller 75 via connections between the catheter 10 and console 60.

Figure 5B:
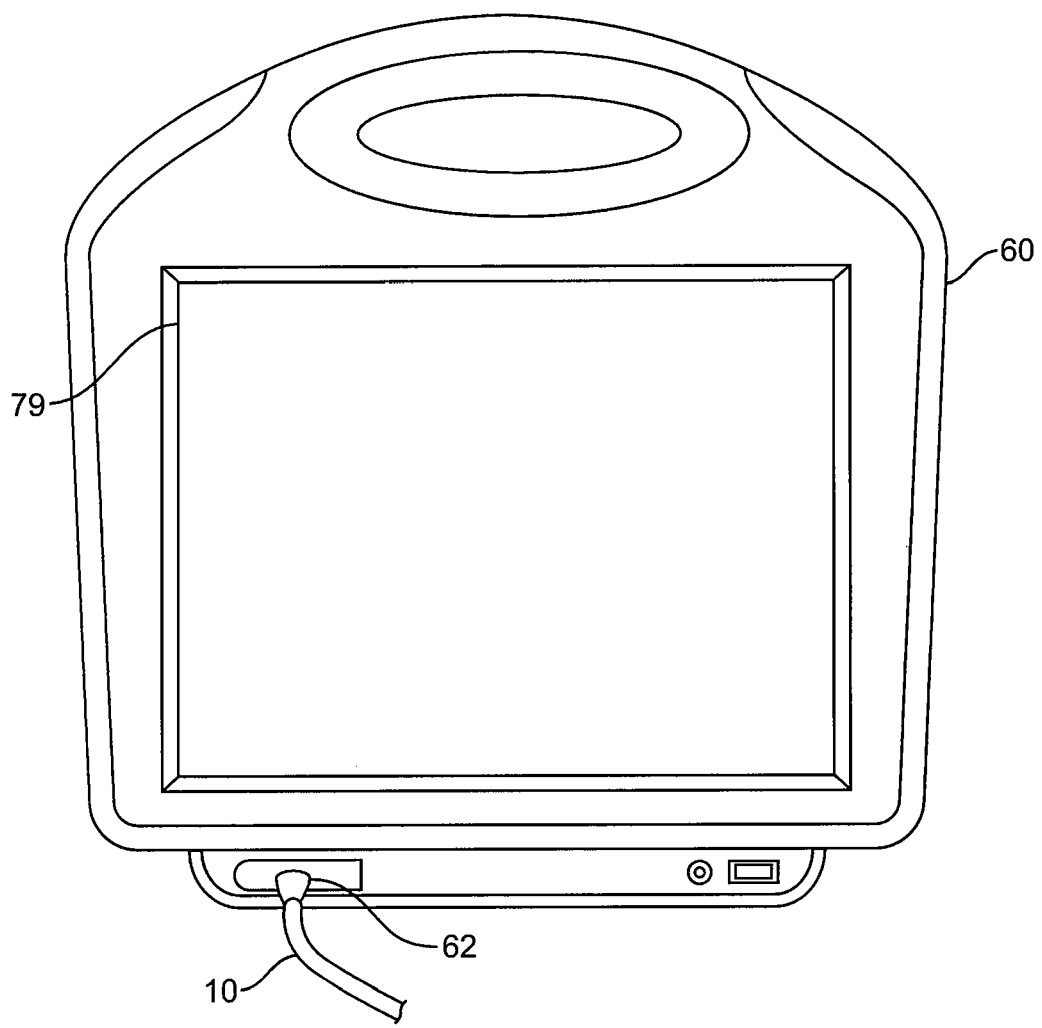

FIG. 5b shows one embodiment of an external console 60 connected to catheter 10. External console 60 optionally comprises a visual display 79 that receives and displays flow and pressure data as sensed by sensors 73 and 74, for example, via a connection 72 to the controller 75. Optionally, visual display 79 is a touch-screen display allowing a user to interact with console 60.

Figure 6A:
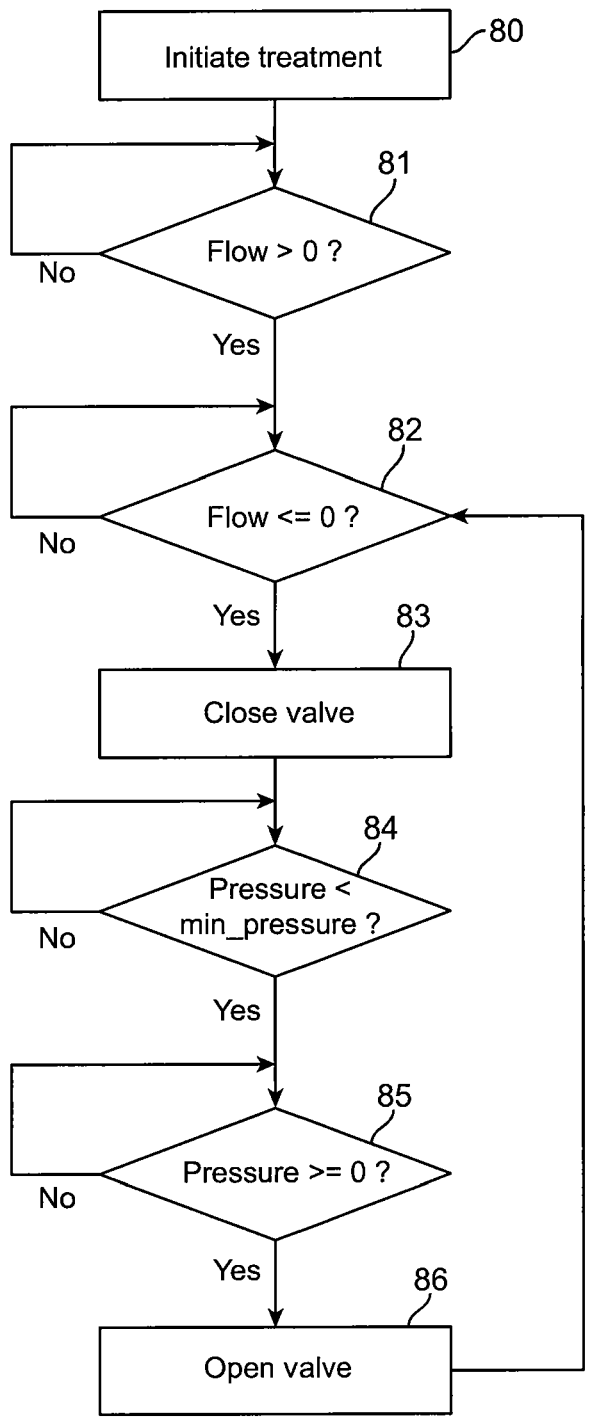
Figure 6B:
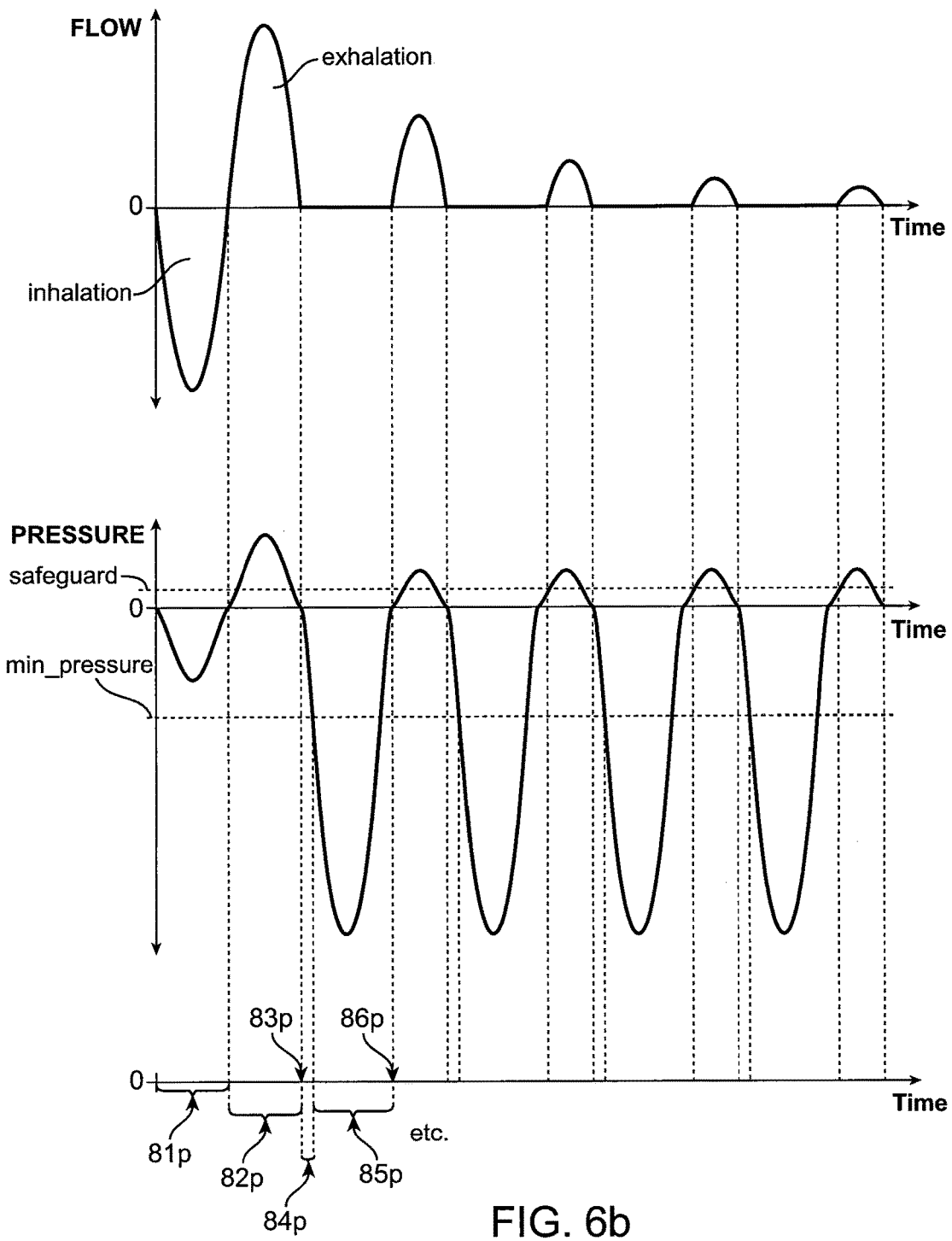

FIGS. 6a and 6b illustrate the operation of one-way flow assembly 70. FIG. 6a is a flowchart showing the operational steps of valve controller 75 as it produces the electrical valve control signal 78 to open or close valve 71 based on input from flow sensor 73 and pressure sensor 74. FIG. 6b is a graph showing exemplary signals generated by the flow sensor 73 (top panel) and pressure sensor 74 (bottom panel) during a series of respiration cycles. The flow and pressure direction during exhalation is herein referred to as the positive flow and pressure direction and plotted on the positive ordinate of the graphs in FIG. 6B, and the flow and pressure direction during inhalation is referred to as the negative flow direction and plotted on the negative ordinate of FIG. 6B.

Initially, the patient may breathe normally through lumen 18 of catheter 10. Once the treatment is initiated (step 80)—which could be accomplished using the visual display 79—valve controller 75 waits for the completion of an inhalation cycle, until flow sensor 73 indicates a flow value that is greater than a specified flow threshold value. This is shown as step 81 in FIG. 6a and shown as the first flow and pressure cycle in FIG. 6B lasting for a period indicated as 81p. The flow threshold value is chosen to indicate the beginning of an exhalation cycle. FIGS. 6a and 6b and the present description assume an exemplary flow threshold value of zero. Optionally, the flow threshold value is configurable to a value other than zero.

In step 82 in FIG. 6a (also indicating the positive flow and pressure in FIG. 6b), valve controller 75 maintains valve 71 in an open state during exhalation until flow sensor 73 receives a flow value less than or equal to zero. Thus, as is illustrated in FIG. 6b, step 82 lasts for a period indicated as 82p as long as flow sensor 73 senses an air flow value greater than zero.

When flow sensor 73 senses a flow value that is less than or equal to zero, valve controller 75 closes valve 71 in step 83 in FIG. 6a and no air flows through the lumen into the lung compartment. As is shown in FIG. 6b, Step 83 occurs contemporaneously with the flow value reaching zero or lower at the point in time denoted 83p. Typically, the flow reduces to zero at the end of exhalation, at which point valve controller 75 closes the valve 71.

The following steps of valve controller 75 refer to a pressure threshold value. The pressure threshold value is chosen to indicate the beginning of an exhalation cycle. This value is configurable, and in what follows, an example pressure threshold value of zero is assumed.

Ideally, it is desirable that valve controller 75 reopen valve 71 when the pressure increases to or above the pressure threshold value. Realistically, given hardware imperfections, the pressure as sensed and reported by pressure sensor 74 at the end of exhalation may fluctuate around zero, causing chatter of valve 71. To prevent valve chatter, in step 84, valve controller 75 maintains valve 71 in a closed state while the pressure remains above a specified minimum pressure value, denoted as min_pressure in FIGS. 6a and 6b. This minimum pressure—min_pressure—is configurable and set to a value appreciably less than the specified pressure threshold value. Thus, as is further shown in FIG. 6b, valve 71 remains closed during the period 84p.

Optionally, during step 84, valve controller 75 also monitors pressure to ensure that valve 71 will open if the patient starts exhalation prior to the pressure decreasing to below min_pressure, To this end, during step 84, valve controller 75 is optionally configured to open valve 71 if pressure increases to a value that is above the pressure threshold value by an amount referred to as a safeguard offset value. The safeguard offset value is configurable.

During step 85 in FIG. 6a, once the pressure passes below "min_pressure", valve controller 75 maintains valve 71 in a closed state until the pressure increases to or passes the pressure threshold value. Referring to FIG. 6b, step 85 lasts the duration between the achievement of min_pressure in step 84 and the attainment of the pressure threshold value, with the period denoted as 85p in FIG. 6b.

When the pressure increases to or passes the pressure threshold value, the valve controller 75 opens the valve 71 at step 86 in FIG. 6a. Thus, referring to FIG. 6b, the opening of the valve in step 86 occurs at point 86p and is contemporaneous with the pressure increasing to or passing a zero value. This allows air to empty from the lung compartment in communication with lumen 18.

Thereafter, as the patient resumes inhalation, the valve controller 75 resumes operation at Step 82 (close valve 71 and prevent airflow into the target lung compartment), for a new respiration cycle, until the lung reduction process is terminated.

Figure 7:
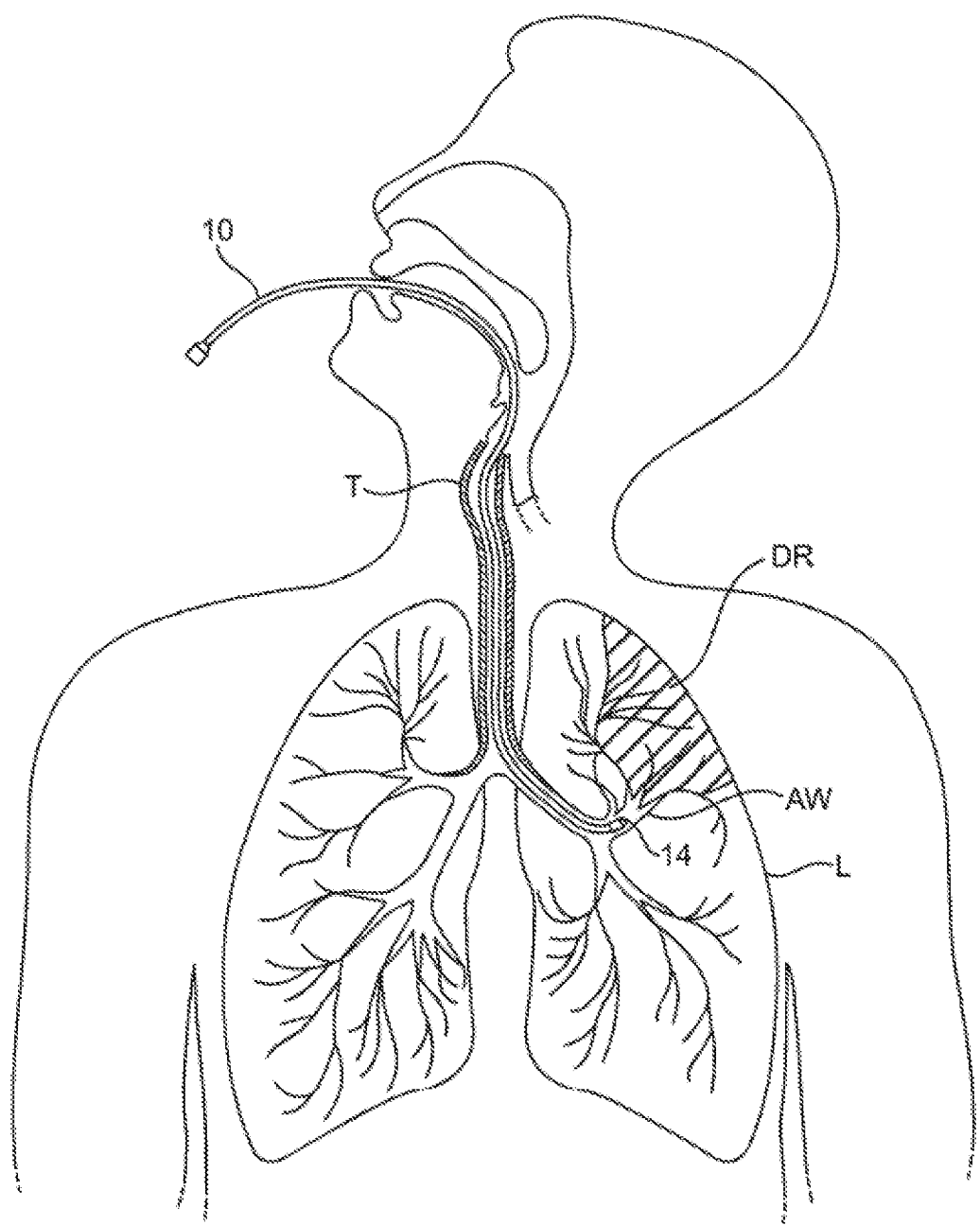
FIG. 7 illustrates the trans-esophageal endobronchial placement of the catheter of FIG. 1 in an airway leading to a diseased lung region in accordance with the principles of the present invention.

Use of the endobronchial lung volume reduction catheter 10 to reduce the residual volume of a diseased region DR of a lung L is illustrated beginning in FIG. 7. Catheter 10 is introduced through the patient's mouth, down past the trachea T and into a lung L. The distal end 14 of the catheter 10 is advanced to the main airway AW leading into the diseased region DR of the lung. Introduction and guidance of the catheter may be achieved in conventional manners, such as described in commonly-owned U.S. Pat. Nos. 6,287, 290; 6,398,775; and 6,527,761, the full disclosures of which are incorporated herein by reference.

Figure 8A:
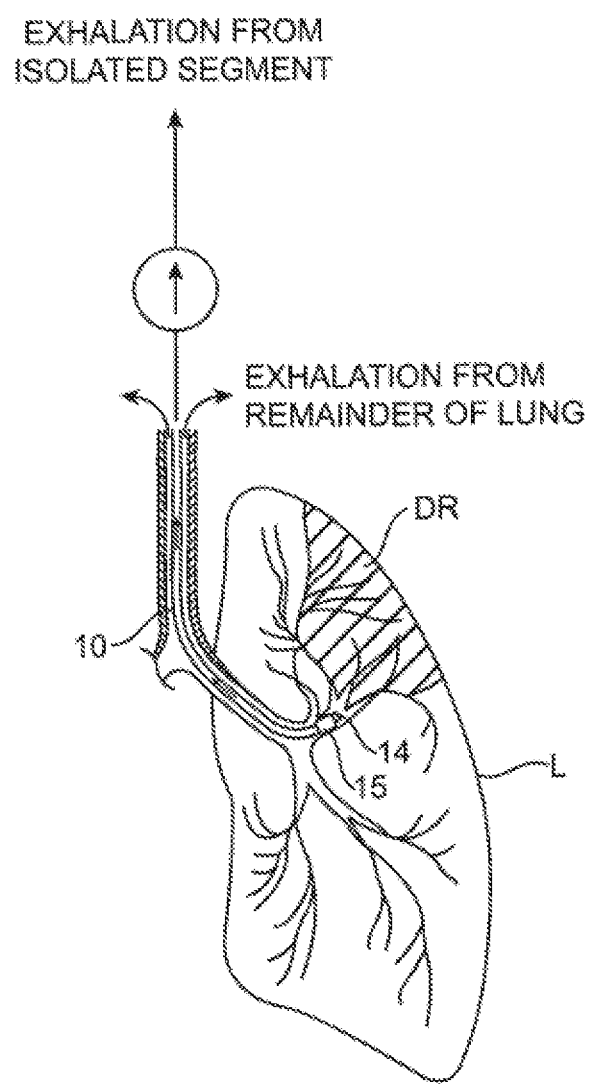
FIGS. 8a-8d illustrate use of the catheter as placed in FIG. 7 for isolating and reduction of the volume of the diseased lung region in accordance with the principles of the present invention.

Referring now to FIGS. 8A-D, functioning of the one-way valve element in achieving the desired lung volume reduction will be described. After the distal end 14 of the catheter 10 is advanced to the feeding airway AW, an expandable occluding element 15 is expanded to occlude the airway. The expandable occluding element 15 may be a balloon, cuff, or a braided balloon as described in copending applications 60/823,734, filed on Aug. 28, 2006, and 60/828,496 filed on Oct. 6, 2006, the full disclosures of which are incorporated herein by reference. At that point, the only path between the atmosphere and the diseased region DR of the lung is through the lumen 18 of the catheter 10. As the patient exhales, as shown in FIG. 8A, air from the diseased region DR flows outwardly through the lumen 18 and the one-way flow element 22, one-way flow assembly 70, or any other one-way flow structure, causing a reduction in residual air within the region and a consequent reduction in volume. Air from the remainder of the lung also passes outward in the annular region around the catheter 10 in a normal manner.

Figure 8B:
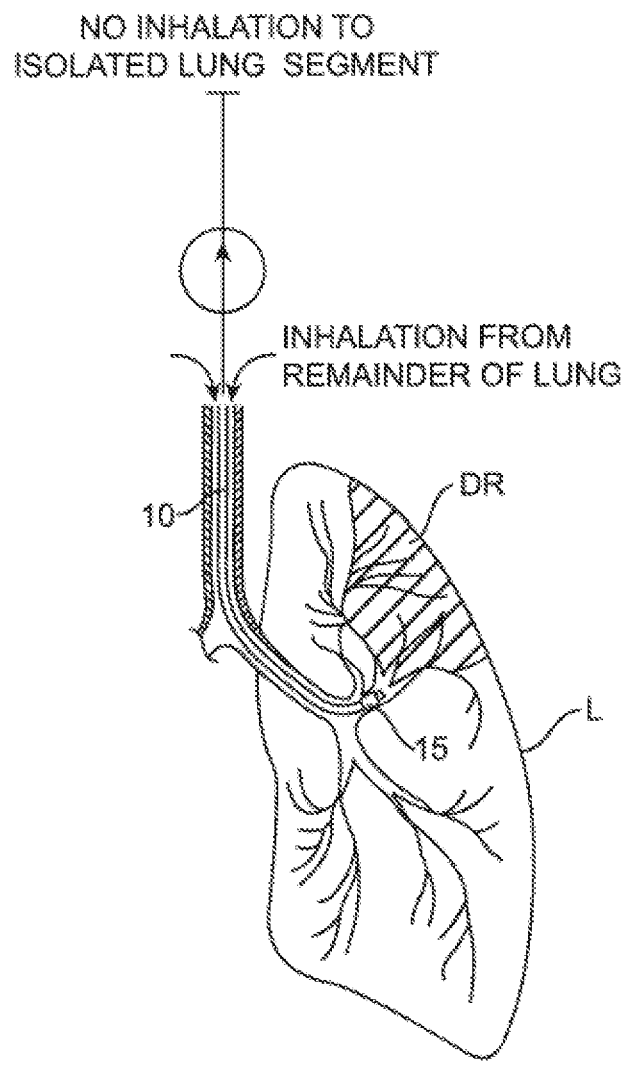
Figure 8C:
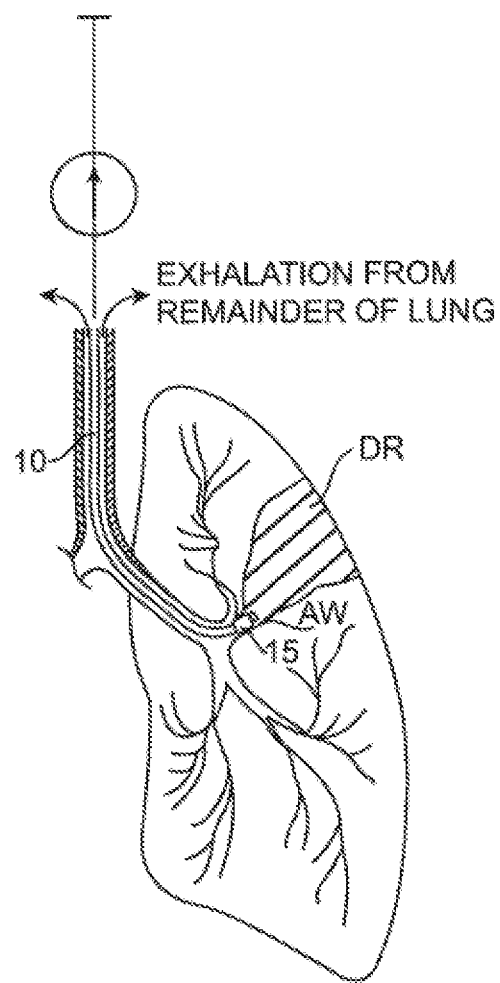
Figure 8D:
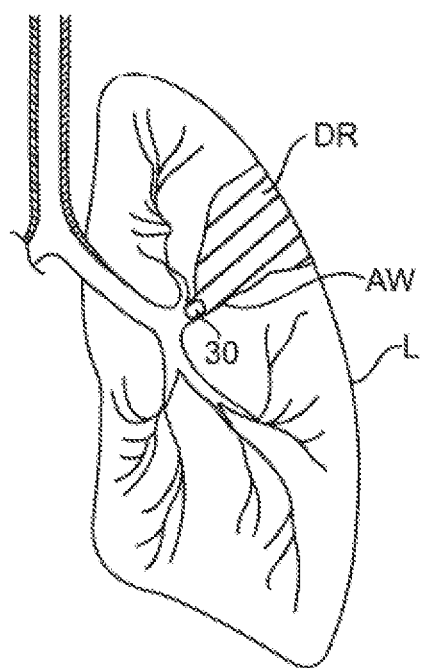

As shown in FIG. 8B, in contrast, when the patient inhales, no air enters the diseased regions DR of the lung L (as long as there are no significant collateral passageways), while the remainder of the lung is ventilated through the region around the catheter. It will be appreciated that as the patient continues to inhale and exhale, the air in the diseased region DR is incrementally exhausted, further reducing the lung volume as the external pressure from the surrounding regions of the lung are increased relative to the pressure within the diseased region. As shown in FIG. 8C, after sometime, typically seconds to minutes, air flow from the isolated lung segment will stop and a maximum or near-maximum level of residual lung volume reduction within the diseased region DR will have been achieved. At that time, the airway AW feeding the diseased region DR can be occluded, by applying heat, radiofrequency energy, glues, or preferably by implanting an occluding device 30, as shown in FIG. 8D. Implantation of the occluding device may be achieved by any of the techniques described in commonly-owned U.S. Pat. Nos. 6,287,290; and 6,527,761, the full disclosures of which have been previously incorporated herein by reference.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A diagnostic catheter comprising:
   a catheter body having a distal end, a proximal end, and a lumen extending from the distal end to the proximal end, wherein at least a distal portion of the catheter body is adapted to be advanced through the airways of the lung; and
   a transparent expandable member disposed near the distal end of the catheter body, wherein the transparent expandable member is adapted to be expanded in an airway leading to a lung compartment, wherein a proximal end of the transparent expandable member is attached to an outer surface of the catheter body and a distal portion of the transparent expandable member is attached to an inner surface of the lumen such that the transparent expandable member forms the wide angle lens.

2. The diagnostic catheter of claim 1, wherein the proximal end of the transparent expandable member is attached circumferentially to the outer surface of the catheter body and the distal portion of the transparent expandable member is attached circumferentially to the inner surface of the lumen.

* * * * *